(12) United States Patent
Peuker et al.

(10) Patent No.: US 9,981,787 B2
(45) Date of Patent: May 29, 2018

(54) DEVICE FOR STORING AND DISPENSING A MATERIAL AND METHOD OF MAKING SUCH A DEVICE

(75) Inventors: Marc Peuker, Schondorf (DE); Andreas Johannes Boehm, Reichling (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 490 days.

(21) Appl. No.: 13/388,235

(22) PCT Filed: Aug. 12, 2010

(86) PCT No.: PCT/US2010/045304
§ 371 (c)(1),
(2), (4) Date: Jan. 31, 2012

(87) PCT Pub. No.: WO2011/025665
PCT Pub. Date: Mar. 3, 2011

(65) Prior Publication Data
US 2012/0129127 A1    May 24, 2012

(30) Foreign Application Priority Data

Aug. 28, 2009 (GB) .................................. 0915006.1

(51) Int. Cl.
*A61C 5/62* (2017.01)
*B65D 47/30* (2006.01)
(Continued)

(52) U.S. Cl.
CPC .............. *B65D 47/305* (2013.01); *A61C 5/62* (2017.02); *A61C 5/64* (2017.02); *A61C 5/68* (2017.02); *B65D 51/222* (2013.01); *B65D 81/325* (2013.01); *B05B 11/0094* (2013.01); *Y10T 29/4998* (2015.01)

(58) Field of Classification Search
CPC .. B65D 51/222; B65D 51/223; B65D 51/228; A61C 5/62; A61C 5/64; A61C 5/68; A61C 9/0026
(Continued)

(56) References Cited

U.S. PATENT DOCUMENTS 2,317,420 A * 4/1943 Taylor ........................... 220/265
2,990,980 A * 7/1961 Gronemeyer ................. 222/536
(Continued)

FOREIGN PATENT DOCUMENTS

| EP | 0 157 121 | 10/1985 | |
|----|-----------|---------|---|
| WO | WO 2007/104037 | 9/2007 | |
| WO | WO 2007104037 A2 * | 9/2007 | ............... A61C 5/06 |

OTHER PUBLICATIONS

International Search Report for International Publication PCT/US2010?045304 dated Nov. 24, 2010.

*Primary Examiner* — Tatiana Nobrega (57) ABSTRACT

A device for dispensing a dental material comprises a container for containing the material and an outlet which is closed by a closure. A breakable seal is arranged between the closure and the container. The device further is operable between a storage position in which the outlet is closed and an operational position in which the outlet is open. An initial operation toward the operational position causes the seal to break, whereby the closure is captured in the device. The device may provide a relatively long shelf life for the material, and may facilitate preparation of the material for use.

9 Claims, 5 Drawing Sheets

(51) Int. Cl.
*A61C 5/68* (2017.01)
*A61C 5/64* (2017.01)
*B65D 51/22* (2006.01)
*B65D 81/32* (2006.01)
*B05B 11/00* (2006.01)

(58) Field of Classification Search
USPC ....... 433/89, 90, 80; 222/81, 83, 137, 145.6, 222/556, 546, 563, 544, 526, 531, 532, 222/537, 541.1, 541.5; 215/228, 251, 252
See application file for complete search history.

(56) References Cited

U.S. PATENT DOCUMENTS

| | | | | |
|---|---|---|---|---|
| 3,251,516 | A * | 5/1966 | Thomas | 222/536 |
| 3,318,494 | A * | 5/1967 | Porter et al. | 222/534 |
| 3,369,719 | A * | 2/1968 | Duke | 222/498 |
| 3,568,895 | A * | 3/1971 | Porter | 222/534 |
| 3,653,546 | A * | 4/1972 | Hazard | 222/83 |
| 3,659,750 | A | 5/1972 | La Vange | |
| 3,680,605 | A | 8/1972 | Nigro | |
| 3,774,822 | A * | 11/1973 | Hazard | 222/541.6 |
| 4,674,661 | A * | 6/1987 | Herold | 222/386 |
| 5,044,525 | A | 9/1991 | McKinney | |
| 5,156,302 | A * | 10/1992 | Kuitems | 222/534 |
| 5,370,273 | A * | 12/1994 | Rohloff et al. | 222/132 |
| 6,375,460 | B1 | 4/2002 | Plaumann | |
| 7,097,078 | B2 * | 8/2006 | Sanchez | 222/402.21 |
| 2002/0170930 | A1 | 11/2002 | Elder | |
| 2008/0203112 | A1* | 8/2008 | Peuker et al. | 222/137 |
| 2009/0298010 | A1* | 12/2009 | Broyles et al. | 433/90 |
| 2010/0206905 | A1* | 8/2010 | Horner et al. | 222/137 |
| 2012/0258422 | A1* | 10/2012 | Leiner et al. | 433/90 |

* cited by examiner

DEVICE FOR STORING AND DISPENSING A MATERIAL AND METHOD OF MAKING SUCH A DEVICE

CROSS REFERENCE TO RELATED APPLICATIONS

This application is a national stage filing under 35 U.S.C. 371 of PCT/US2010/045304, filed Aug. 12, 2010, which claims priority to Great Britain Application No. 0915006.1, filed Aug. 28, 2009, the disclosures of which are incorporated by reference in their entirety herein.

FIELD OF THE INVENTION

The present invention relates to a device for storing and dispensing a material, such as a liquid or pasty dental material. The invention further relates to a method of making the device according to the invention.

BACKGROUND ART

In dentistry various packages are known for storing and/or for dispensing of dental materials. There are, for example, packages that store the material in the form of individual components. Those packages may also allow for mixing of the components in the package prior to use. Some packages further allow the dental materials to be dispensed directly into a patient's mouth.

For example WO 2007/104037 discloses a capsule for storing two material components separated from one another. The capsule further allows for mixing the material components and for dispensing the mixture from a nozzle. The nozzle is pivotable between a closed position in which the capsule is closed and an open position in which the capsule is opened. Thus in the closed position the dental material can be stored in the capsule, and in the open position the material can be mixed and dispensed from the capsule.

Although existing packages may provide for a variety of advantages there is still a desire to provide a package that facilitates application of the dental material. There is further still a desire for a package which is easy to use and which is relatively inexpensive. Desirably a package for dental materials also provides for a relatively long shelf life.

SUMMARY OF THE INVENTION

In one aspect the invention is directed to a device for dispensing a dental material. The device comprises:
  a container for containing the dental material, the container having an outlet which is closed by a closure;
  a breakable seal connecting the closure and the container;
  a valve member;
  the device allowing for a relative movement between the valve member and the outlet between a storage position in which the outlet is closed and an operational position in which the outlet is open;
  wherein the valve member engages with the closure such that a relative movement between the valve member and the outlet also causes a relative movement between the closure and the outlet, whereby the seal is caused to break upon movement toward the operational position; and
wherein the device is adapted to capture the closure in the device in the operational position.

The seal is preferably caused to break upon an initial movement toward the operational position. The initial movement preferably corresponds to a movement between the closure and the outlet at a time at which the breakable seal is still unbroken.

The invention is advantageous in that it may allow for relatively tight encapsulation of the dental material in the device. The invention further may allow reclosing of the device after opening for use. In particular in a device which stores individual components cross-contamination between the components may be avoided due to the reclosing function. Preferably the device when reclosed provides for a relatively tight encapsulation of the dental material. Therefore the device of the invention may allow for storing the dental materials over a relatively long time, for example several months or years, with the breakable seal being still unbroken. Nevertheless the device of the invention may also provide a relatively long storage time for the materials once it was opened and reclosed. The device of the invention is further advantageous in that it is easy to use, for example because it may provide for automatically breaking the seal along with operating the device toward the operational position for the first use. Further due to the closure being captured no part may be lost from the device during use. This may particularly be advantageous for dental and/or medical use in which loose parts at dispensing devices are typically undesirable.

In one embodiment the closure forms one piece with the container. For example the closure, the breakable seal and the container may be integrally molded. The breakable seal may in this case be formed by a relatively thin wall between the container and the closure. Alternatively the closure and the container may form two separate pieces, and the breakable seal may be formed by a non-permanent bond between the container and the closure. A non-permanent bond may for example provided by a non-permanent or breakable adhesive. The skilled person will recognize other appropriate solutions to provide a breakable seal.

In one embodiment the thinnest wall thickness of the connection between closure and the container is between about 0.05 mm to 0.3 mm, preferably about 0.15 mm. Thus a tight seal may be achieved with the seal being still breakable at acceptable forces.

In another embodiment the device is further adapted to reclose the outlet. This may be achieved in that the device allows for the closure and the outlet to be repositioned toward one another by moving the valve member and the outlet relative to each other from the operational toward the storage position. Therefore the device may allow encapsulating the dental material so that the material can be stored over a relatively long time although the device was opened before.

In one embodiment the device has a piston which is receivable in the container for advancing the material toward the outlet. The container may extend along a longitudinal axis of the device. The container further has preferably at least one chamber for holding the dental material. The chamber may extend generally parallel to the longitudinal axis and may be adapted to receive the piston. The piston is preferably movable in the device in a direction parallel to the longitudinal axis. The chamber may have a rear end which is closed by the piston and an opposite front end accommodating the outlet.

In one embodiment the valve member has a receptacle. The receptacle is preferably adapted to receive at least a part of the closure. Preferably in the storage position the closure covers the outlet and extends in a direction generally parallel to the longitudinal axis from the container into the receptacle. The receptacle may for example be a blind hole in the valve member. In the storage position the opening of the blind hole may be oriented toward the outlet.

In a further embodiment the receptacle has inner side walls which generally correspond in shape to lateral outer side walls of the closure. For example the receptacle and the closure may be generally cylindrical and sized to fit, for example tightly fit, with one another. Thus the closure may be retained in the receptacle by friction. This may provide for capturing the closure in the device in the operational position.

The receptacle may further have a structured side wall which provides retention for a closure having complementary structures. Thus the closure and the receptacle may be shaped to form a positive fit relative to one another. Such a positive fit may provide an interlock, for example a permanent interlock, between the closure and the valve member. Such an interlock is preferably provided in at least a dimension parallel to the longitudinal axis with respect to the device in the storage position. This may provide for relatively secure capturing of the closure in the device in the operational position.

A permanent interlock for the purpose of the invention preferably is only releasable by damaging at least one of the interlocked parts.

In one embodiment the device is adapted to allow for a relative movement between the receptacle and the outlet in a direction generally transverse to the longitudinal axis. Thus the closure, engaged by the receptacle in the valve member, may be sheared from the container when the valve member and the outlet are initially moved relative to each other toward the operational position. Shearing of the closure and the container may provide for relatively low forces for breaking the seal. Therefore the operation of the device may be facilitated for a user.

In a further embodiment the device is adapted to allow for a rotation between the valve member and the outlet. Thus a rotational relative movement between the receptacle and the outlet may be provided. This configuration may allow for a relatively compact design of the device. The rotation axis may for example be arranged substantially transverse to the longitudinal axis. Further the rotation axis may be arranged substantially parallel to the longitudinal axis.

However the device may also be adapted to allow for a linear movement between the valve member and the outlet in a direction generally transverse to the longitudinal axis. This configuration may for example allow a user to easily recognize the position of the valve member from outside the device. Therefore this configuration may facilitate an assessment for the user about whether the device is in the storage or the operational position. The skilled person will be able to provide further arrangements allowing for a relative movement between the valve member and the outlet which likewise provide for operating the device between the storage and the operational position. In particular the rotation axis may be inclined relative to the longitudinal axis, or the linear movement may be allowed in an angle relative to the longitudinal axis.

In one embodiment the device has two chambers for containing the dental material in the form of components for forming a mixture. Each of the chambers preferably has an outlet with an associated closure. Further the valve member in this embodiment preferably has a receptacle for each of the closures. The skilled person further will recognize that two or more valve members may be used in cooperation with two or more chambers, outlets and closures.

The device may further have a dispensing nozzle for dispensing a mixture of the components. The dispensing nozzle may form one part with the valve member. A passageway may extend between the valve member and the nozzle. The passageway may be arranged in the device such that in the operational position the passageway is in fluid communication with the outlet(s). Further the passageway may be arranged in the device such that the fluid communication with the outlet is interrupted in the storage position. The passageway further may have a dispensing opening adjacent a free end of the nozzle. The nozzle may comprise a static mixer for mixing the components, for example the mixer may be accommodated in the passageway. A static mixer is for example available from the Sulzer Chemtech Company, Switzerland under the designation Quadro™ mixer. Therefore the device may be adapted to store the dental material in the form of individual components, and thereby may provide a relatively long storage time for the material. Further the device preferably allows the components to be merged or mixed as the components are dispensed from the device, which may facilitate the preparation of the material for use.

In another embodiment the device is adapted to be received in an applicator for dispensing the dental material. For example the device may have a flange which protrudes from the device laterally to the longitudinal axis and which may be engaged by an applicator. An appropriate applicator is for example available under the designation "Capsule Dispenser" from 3M ESPE, Germany. The applicator may convert a hand force applied by a user for dispensing material into an increased extrusion force for advancing the material in the device. Therefore the maximum hand force may be reduced to a level which is convenient for a user.

The device may contain a light-curable and/or chemically-curable material selected from among:
   a resin modified glass ionomer material,
   a resin modified luting material,
   a resin modified core build-up material,
   a resin based luting material,
   a resin based filling material,
   a resin based core build-up material, and
   a temporary crown and bridge material.

In another aspect the invention relates to a method of making the device according to the invention. The method may comprise the steps of:
   providing a valve member which has a receptacle;
   molding a container for containing the material and a closure for an outlet in the container, and thereby shaping outer walls of a closure by inner walls of the receptacle.

In one embodiment the method comprises the step of providing a first core and a second core which are movable relative to one another. The first core may be adapted to shape at least an inner wall portion of the chamber of the device. Further the second core may be adapted to shape at least an inner wall portion of the outlet. The first and second cores each may have a free end. The second core may be arranged at least partially within the first core, for example the first and second cores may be generally cylindrical with the first core having a hole for receiving the second core. Thus the first and second cores are preferably movable relative to each other and preferably adapted for guiding each other.

The method may further comprise the steps of:
(a) providing a mold;
(b) providing the valve member in the mold;

(c) positioning the first and second core in the mold with the free end of the second core abutting the valve member and with the first core spaced from the valve member;

(d) providing a flowable hardenable plastic material into the mold; and (e) retracting the second core from the valve member so as to allow the plastic material to flow between the valve member and the second core, and thereby mold the closure.

In an embodiment the steps of the method are performed in the order (a), (b), (c), (d) (e). The method may allow supporting the cores in the mold when plastic material is initially injected into the mold, because the second core may abut the valve member and the first core is guided by the second core. During filling of the mold the flowing plastic material may cause a non-uniform pressure to the cores which in response may cause a deformation of the cores. However because the cores are supported by the valve member at the stage of filling the mold such bending of the cores due to non-uniform pressure may be prevented. Further a retraction of the second core when the mold is already filled with plastic material may allow for molding the closure, substantially without causing the cores to deform or bend. This is because at that stage the cores may be already surrounded by plastic material and may therefore be generally uniformly pressurized in different dimensions by the plastic material.

In one embodiment suitable plastic materials for the valve member may be selected from among polycarbonate (PC), polystyrene (PS), polybutylene terephthalate (PBT), acrylonitrile butadiene styrene (ABS), polyoxymethylene (POM), polypropylene (PP), polyethylene (PE), and polyamide (PA).

In another embodiment suitable plastic materials for the container may be selected from among polypropylene (PP), polyethylene (PE), acrylonitrile butadiene styrene (ABS), and polyoxymethylene (POM).

The plastic material may further be glass or carbon fiber reinforced. Furthermore a grade of these plastic materials may be used having a higher tensile strength relative to the standard grades.

DETAILED DESCRIPTION OF THE INVENTION

Figure 1:
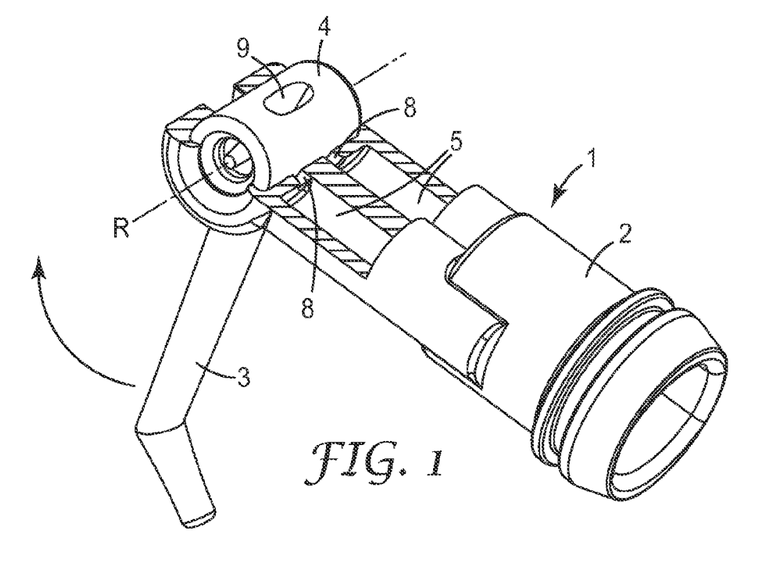
FIG. 1 is a perspective view of a device for dispensing a dental material.

FIG. 1 shows a device 1 for dispensing a dental material. The device 1 has a container 2 for storing a dental material and a nozzle 3 for dispensing the material. The device is shown in a closed position in which the dental material is encapsulated within chambers 5 in the container 2. In the example shown the container 2 has two chambers 5 for containing components of a dental material which may be mixed to form a dental composition. The chambers 5 are closed at one end by pistons (not shown) which are received in the chambers 5 and which can be moved to advance the components toward the nozzle. Further the chambers 5 each have an outlet 8 which in the situation shown are blocked or closed as described in more detail below. A passageway 9 is provided in the device for dispensing the dental material. The passageway 9 extends through the valve member 4 and the nozzle 3. In the closed position shown an opening of the passageway 9 is offset from the outlets 5 so that the material in the chambers is prevented from reaching the passageway 9. The valve member 4 in this example is rotatable to an open position (indicated by the arrow) about an axis R to bring the outlets 8 in fluid communication with the passageway 9 of the nozzle 3. In the open position the device can be used to dispense the dental material, for example directly into a patient's mouth. A static mixer (not shown) may be arranged in the passageway 9 for mixing the components as they are dispensed through the nozzle 3.

Figure 2A:
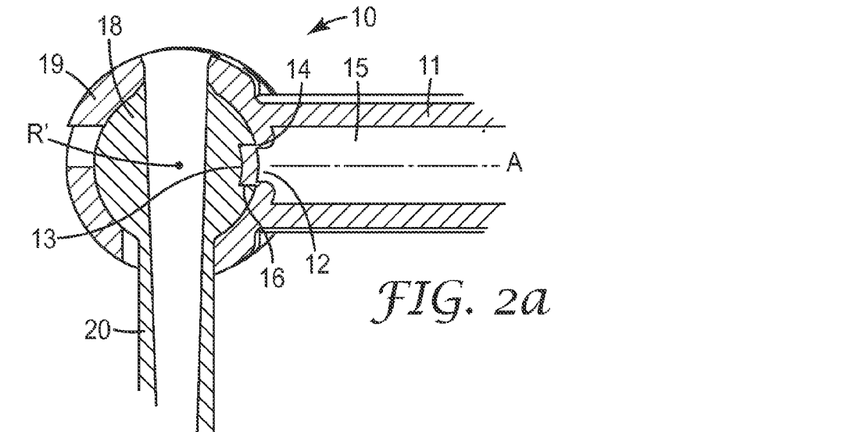
FIGS. 2a, 2b are cross-sectional views of a device for dispensing a dental material according to an embodiment of the invention.
Figure 2B:
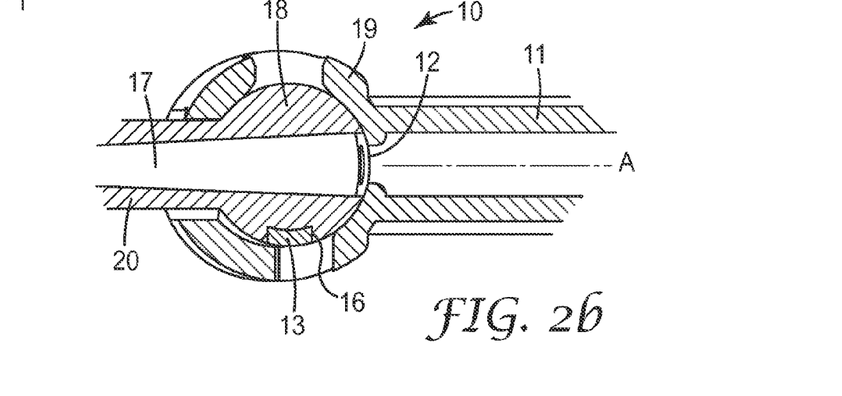

FIGS. 2a and 2b are cross-sectional views of embodiments of the invention at two different operational stages.

FIG. 2a shows a device 10 that has a container 11 for containing the dental material and a nozzle 20 for dispensing the dental material. The container 11 has a chamber 15 and an outlet 12 for the material. The device 10 further has a first valve member 18 which is preferably connected to the nozzle 20. The first valve member 18 is movably arranged in a second valve member 19 which in the example shown is formed by a portion of the container 11. Therefore the first and second valve members 18, 19 are movable, in the example rotatable, relative to one another. The first and second valve members 18, 19 are in particular rotatable relative to each other about a rotation axis R' (perpendicular to the plane of the Figure) which is arranged substantially perpendicular to a longitudinal axis A of the device 10. The longitudinal axis A preferably extends substantially parallel to a direction in which a piston of the device (not shown) is movable for extruding material from the device. In the situation shown in FIG. 2a the first valve member 18 and the outlet 12 are positioned relative to one another in a storage position in which the outlet 12 is closed. In particular the outlet 12 is closed by a closure 13. The closure 13 is connected with the container via a breakable seal 14. The breakable seal 14 preferably provides for a relatively tight seal of the outlet, but can be broken for removing the closure 13 from the outlet 12. The closure 13 protrudes along the longitudinal axis A from the container 11 into a receptacle 16 in the first valve member 18. Thus the closure 13 is engaged with the first valve member 18. A force applied to cause the relative movement between the first valve member 18 and the outlet 12 therefore also puts the closure 13 under load and causes the breakable seal to break as a certain minimum force is reached. When the breakable seal is broken the movement is enabled between the first valve member 18 and the outlet 12. Because the closure 13 is engaged by the first valve member 18 a movement of the first valve member 18 relative to the outlet 12 also causes a movement of the closure 13 relative to the outlet 12.

FIG. 2b shows the device 10 in the operative position. The outlet 12 is in fluid communication with a passageway 17 in the valve member 18. The passageway 17 preferably extends through the valve member 18, and through the nozzle 20.

Therefore in the situation shown the device 10 may be used to dispense the dental material from the device 10. The closure 13 is still received in the receptacle 16 of the device 10. Further the closure 13 is captured in the device 10, in the example between the first and second valve members 18, 19. Therefore the closure 13 can be repositioned for reclosing the outlet 12 by relative movement between the first valve member 18 and the outlet 12 toward the storage position. The dental material thus is preferably prevented from exiting the outlets.

Therefore the material may be prevented from flowing between the first and second valve members 18, 19 which, for example when the material dries or hardens, may cause the valve members 18, 19 to adhere to one another, thus hindering a movement of the valve members relative to one another. Therefore the device may be used for multiple applications, and may allow for sealing the material in the device between two applications.

The closure 13 and the container 11 may for example be formed in one piece, for example integrally molded.

Figure 3A:
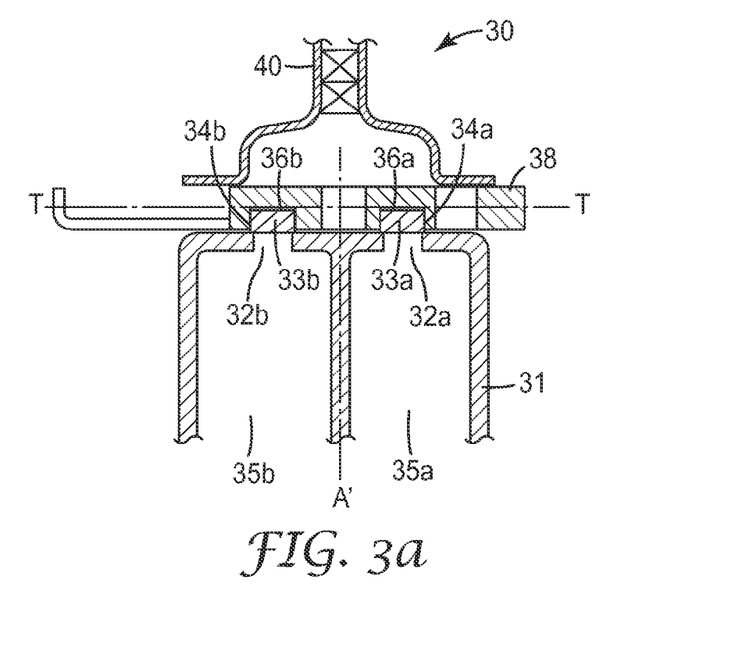
FIGS. 3a, 3b are cross-sectional views of a device for dispensing a dental material according to a further embodiment of the invention.
Figure 3B:
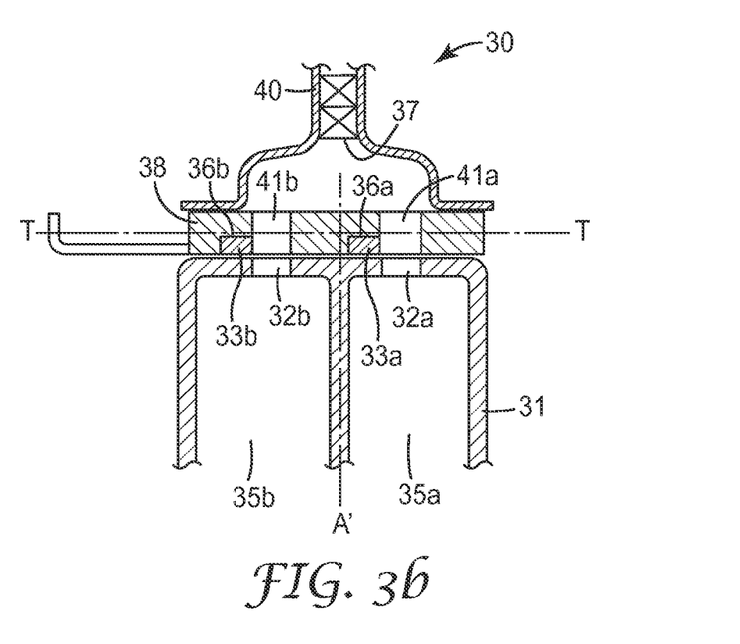

FIGS. 3a and 3b are cross-sectional views of another embodiment according to the invention at two different operational stages.

FIG. 3a shows a device 30 having a container 31 for containing individual components of the dental material and a nozzle 40 for dispensing the dental material. The container 31 has a first and a second chamber 35a, 35b. The first chamber 35a has a first outlet 32a, and the second chamber 35b has a second outlet 32b. The device 30 further has a valve member 38. The valve member 38 is movably arranged relative to the container 31. In particular the valve member 38 is arranged adjacent a front face of the container 31 which comprises the first and second outlets 32a, 32b. In the example the valve member 38 is movably arranged between the container 31 and the nozzle 40, however the nozzle 40 may also be connected to the valve member 38 or may be part of it. The valve member 38 and the container 31 in the illustrated example are linearly movable relative to one another along an axis T which is arranged substantially perpendicular to a longitudinal axis A' of the device 30. As in the previous example the longitudinal axis A' preferably extends substantially parallel to a direction in which a piston of the device (not shown) is movable for extruding material from the device. FIG. 3a illustrates a situation in which the valve member 38 and the outlets 32a, 32b are positioned relative to one another in a storage position in which the outlets 32a, 32b are closed. In particular the first outlet 32a is closed by a first closure 33a, and the second outlet 32b is closed by a second closure 33b. The closures 33a, 33b are connected with the container via a first and second breakable seals 34a, 34b, respectively. The first and second closures 33a, 33b protrude from the container 31 along the longitudinal axis A' into respective first and second receptacles 36a, 36b in the valve member 38. Thus the closures 33a, 33b are engaged with the valve member 38 so that a force applied to move the valve member 38 and the outlets 32a, 32b relative to each other causes the breakable seal to break upon reaching a certain minimum force. This also enables the valve member 38 and the outlets 32a, 32b to be moved relative to one another. The closures 33a, 33b due to the engagement with the valve member 38 also move relative to the outlets 32a, 32b when the valve member 38 and the outlets 32a, 32b are moved relative to one another.

FIG. 3b shows the device 30 in the operative position. The first and second outlets 32a, 32b are in fluid communication with first and second conduits 41a, 41b respectively, and the conduits 41a, 41b establish a fluid communication between the outlets 32a, 32b and a passageway 37 in the nozzle 40. Therefore in the situation shown the device 30 may be used to dispense the dental material from the device 30. The closures 33a, 33b are still received in the receptacles 36a, 36b of the device 30, and therefore captured in the device 30. In the example the closures 33a, 33b are captured between the valve member 38 and the container 31. This allows the closures 33a, 33b to be repositioned for reclosing the outlets 32a, 32b when the device is reset toward the storage position. Therefore the material components are preferably kept inside the outlets so that cross-contamination of the material components due to mutual contact outside the outlets is prevented. Further the material may be prevented from flowing between the first and second valve members which otherwise may cause the mobility of the valve members relative to each other to be hindered, for example if chemically reacting, for example hardenable, materials are used. Therefore the device preferably can be used to store and dispense chemically reacting, for example hardenable, materials.

Also in this embodiment the closures 33a, 33b and the container 31 may be formed in one piece, for example integrally molded.

Figure 4A:
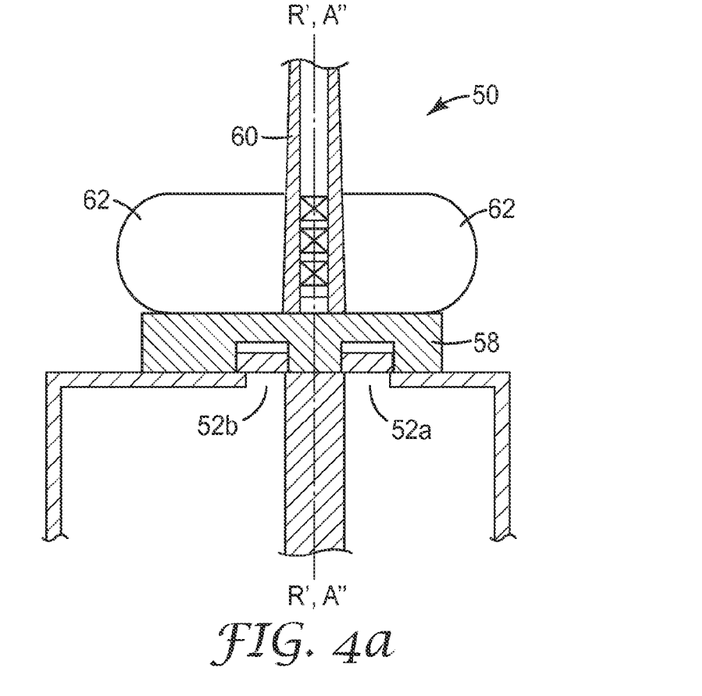
FIGS. 4a, 4b are cross-sectional views of a device for dispensing a dental material according to still a further embodiment of the invention.
Figure 4B:
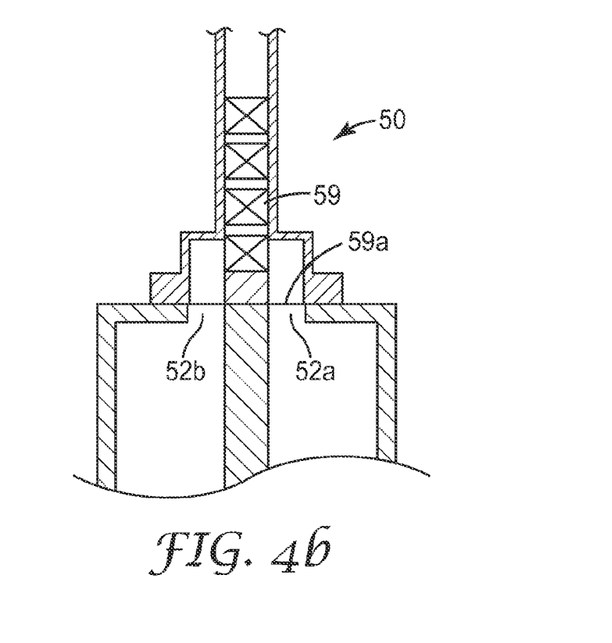

FIGS. 4a and 4b are cross-sectional views of another embodiment according to the invention at two different operational stages. The embodiment shown generally corresponds to the embodiment shown in FIG. 3a and FIG. 3b, but differentiates in that it has a valve member 58 and outlets 52a, 52b which are movable about a rotation axis R' relative to one another. The rotation axis R' in this embodiment is arranged parallel or inline with a longitudinal axis A'' of the device. Further the device 50 shown has a nozzle 60 which is connected or forms one piece with the valve member 58. The valve member 58 further provides one large opening 59a (shown in FIG. 4b) for cooperation with the first and second outlets 52a, 52b. The opening 59a corresponds to an end of a passageway 59 through which the material may be dispensed. A rotational movement of the valve member and the outlets relative to each other may allow for a relative compact design of the device for example. The nozzle 60 in the example shown further has optional wings 62. The wings 62 may allow a user to conveniently operate the nozzle for setting the device between the storage and the operational position.

Figure 5A:
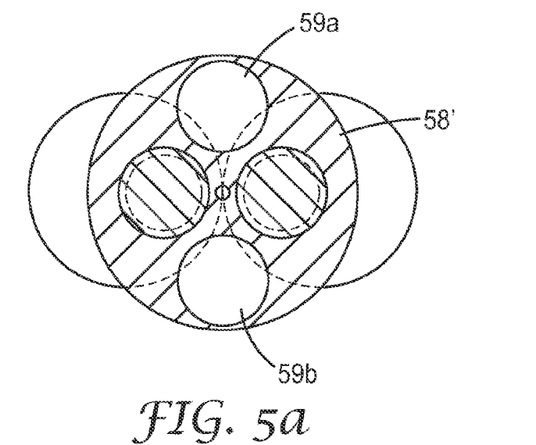
FIGS. 5a, 5b are cross-sectional top views of the device shown in FIGS. 4a and 4b respectively.
Figure 5B:
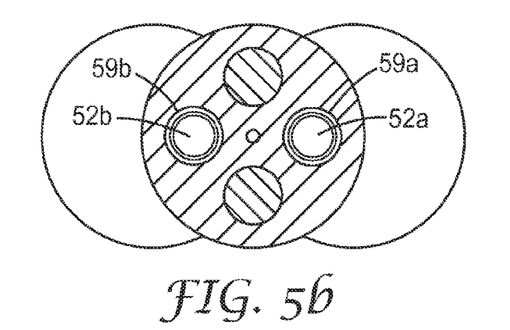

FIGS. 5a and 5b are cross-section top views of the device shown in FIGS. 4a and 4b, respectively, but with an alternative valve member 58'. The valve member 58' instead of on large opening has two openings 59a, 59b which can be brought in alignment with outlets 52a, 52b of the device for establishing the operational position of the device. Separate openings instead of one large opening may for example reduce the risk for cross-contamination between individual components stored in the device.

Figure 6:
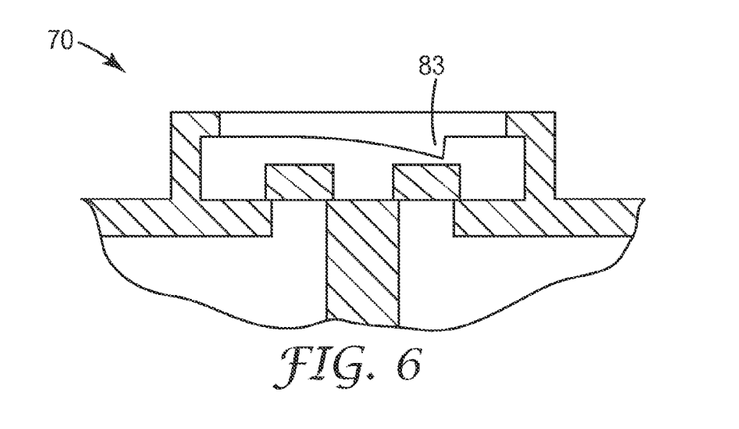
FIG. 6 is a cross-sectional view of a device for dispensing a dental material according to another embodiment of the invention.

FIG. 6 shows a device 70 which generally corresponds to the embodiments shown in FIGS. 4a, 4b and FIGS. 5a, 5b. The device 70 has a retention element 83 for cooperating with a corresponding retention element in the valve member (not shown). The retention element preferably allows a fixation of the valve member and the container in the storage and/or the operational position. This may provide a tactile and/or audible signal to a user indicating a proper position of the valve member and the container relative to one another. Further the valve member and the container may be retained in either the storage and/or the operational position(s). This may facilitate the use of the device, and may further reduce possibilities of improper operation.

Figure 7A:
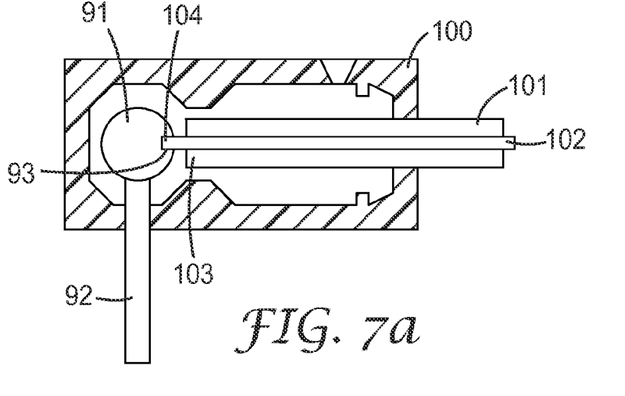
FIGS. 7a-7c are cross-sectional views of a mold for making a device of the invention at different stages of a method according to an embodiment of the invention.
Figure 7B:
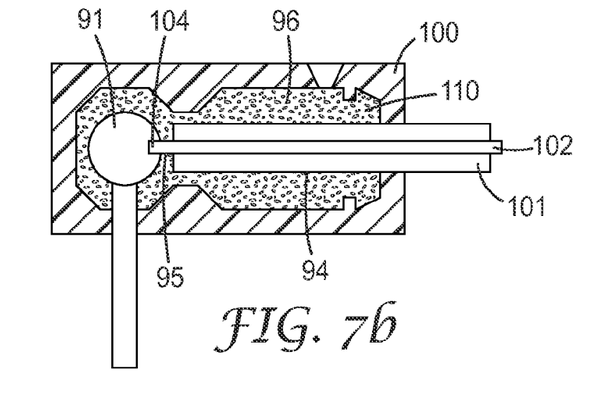
Figure 7C:
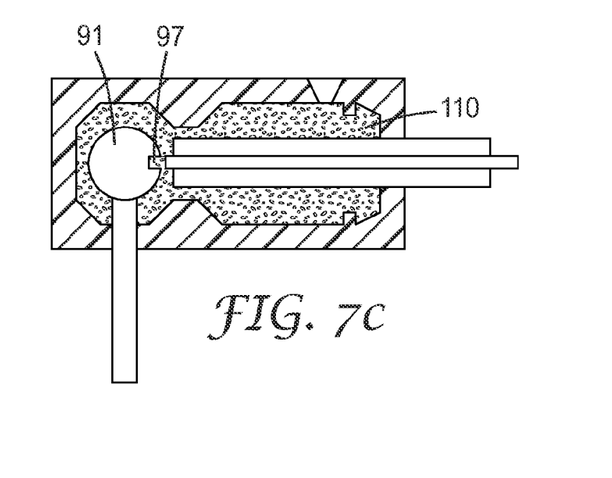

FIGS. 7a to 7c illustrate a method of making a device according to the invention.

FIG. 7a shows a mold 100 in which a valve member 91 is disposed. The valve member 91 in the example is a part with a nozzle 92. The valve member is preferably fixed in the mold. Further a first core 101 and a second core 102 are arranged in the mold. The first and second cores 101, 102 are elongated and have first and second free ends 103, 104 respectively. The second free end 104 abuts the valve member 91, and in particular preferably protrudes into a receptacle 93 of the valve member 91. The first free end 103 is spaced from the valve member 91. The cores 101, 102 and the mold 100 are preferably movable relative to each other to allow a molded device to be removed from the mold and the cores.

In FIG. 7b the mold 100 is filled with a plastic material 110 which at the stage shown is flowable, for example molten from a thermoplastic material. The first free end 104 abuts the valve member 91 and thus preferably seals with the valve member 91 so that plastic material is prevented from penetrating between abutting surfaces of the second core 102 and the valve member 91. The second core 102 is supported at its free end 104 because free end 104 abuts the valve member 91. Further the first core 101 is guided by the second core 102. Therefore the cores 101, 102 may be prevented from deforming, for example bending, during the flowable plastic material 110 is injected into the mold. This may help reducing tolerances during manufacturing, for example. At this stage a chamber 94 and an outlet 95 is shaped in a container 96, but a closure is not present.

In FIG. 7c the second core 102 is retracted over a short distance so that a space is created between the valve member 91 and the second free end 104 of the second core 102. Because the plastic material 110 at this stage is preferably still flowable, for example has not cooled sufficiently for hardening, the space fills by the plastic material 110 so that the closure 97 is formed. During molding the closure 97 the cores 101, 102 are laterally surrounded by plastic material so that pressure required to fill the space applies generally homogeneously on the lateral surfaces of the cores. Therefore the cores are substantially free of lateral forces during molding of the closure, which helps preventing the cores from bending also at this stage. Thus the method of the invention helps to achieve small tolerances during molding a breakable seal. Therefore a series of breakable seals made by the method of the invention may break reliably at relatively constant forces.

We claim:

1. Device for dispensing a dental material, comprising:
    a container for containing a dental material, the container having an outlet which is closed by a closure;
    a breakable seal connecting the closure and the container;
    a valve member;
    the device allowing for a relative movement between the valve member and the outlet between a storage position in which the outlet is closed and an operational position in which the outlet is open;
    wherein the valve member engages with the closure such that the relative movement between the valve member and the outlet also causes a relative movement between the closure and the outlet, whereby the seal is caused to break upon movement toward the operational position;
    wherein the valve member has a receptacle, and wherein in the storage position the closure covers the outlet and extends in a direction generally parallel to a longitudinal axis of the device from the container into the receptacle;
    wherein the receptacle has inner side walls which correspond in shape to outer side walls of the closure;
    wherein the closure is retained in the receptacle by friction; and
    wherein the device is adapted to capture the closure in the device in the operational position.

2. The device of claim 1, wherein the device is adapted to reclose the outlet, in that the device allows for the closure and the outlet to be repositioned toward one another by moving the valve member and the outlet relative to each other from the operational toward the storage position.

3. The device of claim 1, wherein the receptacle and the closure are shaped to form a positive fit with each other, such that an interlock between the closure and the valve member is provided.

4. The device of claim 1, allowing for a relative movement between the receptacle and the outlet in a direction generally transverse to the longitudinal axis.

5. The device of claim 4, allowing for a rotation between the valve member and the outlet about a rotation axis.

6. The device of claim 5, in which the rotation axis is arranged substantially transverse to the longitudinal axis.

7. The device of claim 1, having a piston which is receivable in the container for advancing the material toward the outlet.

8. The device of claim 1, having two chambers for containing a dental material in the form of components for forming a mixture, and a dispensing nozzle that comprises a static mixer for mixing the components.

9. The device of claim 1, wherein the closure and the container are formed by one piece.

\* \* \* \* \*